United States Patent
Ostafin et al.

(10) Patent No.: US 9,415,021 B2
(45) Date of Patent: Aug. 16, 2016

(54) SYNTHESIS OF OXYGEN CARRYING, TURBULENCE RESISTANT, HIGH DENSITY SUBMICRON PARTICULATES

(71) Applicant: Nanoshell Company, LLC, North Salt Lake, UT (US)

(72) Inventors: Agnes Ostafin, North Salt Lake, UT (US); Hiroshi Mizukami, Pasadena, CA (US)

(73) Assignee: NANOSHELL COMPANY, LLC, North Salt Lake, UT (US)

( * ) Notice: Subject to any disclaimer, the term of this patent is extended or adjusted under 35 U.S.C. 154(b) by 0 days.

(21) Appl. No.: 14/711,652

(22) Filed: May 13, 2015

(65) Prior Publication Data
US 2015/0238432 A1    Aug. 27, 2015

Related U.S. Application Data

(63) Continuation-in-part of application No. 13/322,757, filed as application No. PCT/US2010/046417 on Aug. 24, 2010, now abandoned.

(60) Provisional application No. 61/236,810, filed on Aug. 25, 2009.

(51) Int. Cl.
| | | |
|---|---|---|
| *A61K 31/01* | (2006.01) | |
| *A61K 9/51* | (2006.01) | |
| *A61K 38/42* | (2006.01) | |

(Continued)

(52) U.S. Cl.
CPC ............. *A61K 9/5192* (2013.01); *A61K 9/0026* (2013.01); *A61K 9/5115* (2013.01); *A61K 9/5146* (2013.01); *A61K 31/01* (2013.01); *A61K 38/42* (2013.01); *A61K 9/5073* (2013.01); *A61K 9/5123* (2013.01)

(58) Field of Classification Search
CPC ..................................................... A61K 31/01
See application file for complete search history.

(56) References Cited

U.S. PATENT DOCUMENTS

| 4,387,848 A | 6/1983 | Kellogg et al. |
|---|---|---|
| 4,479,790 A | 10/1984 | Bocckino et al. |
| 5,386,734 A | 2/1995 | Pusinelli |

(Continued)

FOREIGN PATENT DOCUMENTS

| CA | 1298822 | 4/1992 |
|---|---|---|
| CN | 101172207 | 5/2008 |

(Continued)

OTHER PUBLICATIONS

Andres, et al., "Anisotropic Calcium Phosphate Nanoparticles Coated with 2-Carboxyethylphosphonic Acid", J Mater. Chem. vol. 16, 2006, 3964-3968.

(Continued)

*Primary Examiner* — Benjamin Packard
(74) *Attorney, Agent, or Firm* — Peacock Myers, PC; Janeen Vilven

(57) ABSTRACT

An artificial oxygen carrier (AOC) for use as a blood substitute in the body. A first gas permeable shell encloses an oxygen carrying agent. The first gas-permeable shell has a second oxygen carrying agent surrounding it, and there is a second gas-permeable shell enclosing the second agent. The concentric shells are not subject to turbulent breakup, or chemical decomposition, and do not release the oxygen carrying agents into the blood.

18 Claims, 5 Drawing Sheets

(51) Int. Cl.
*A61K 9/00* (2006.01)
*A61K 9/50* (2006.01)

(56) References Cited

U.S. PATENT DOCUMENTS

| | | | |
|---|---|---|---|
| 5,635,207 | A | 6/1997 | Grinstaff et al. |
| 5,641,622 | A | 6/1997 | Lake et al. |
| 5,663,051 | A | 9/1997 | Vlasselaer |
| 5,679,394 | A | 10/1997 | Long, Jr. et al. |
| 5,811,521 | A | 9/1998 | Kluger et al. |
| 5,840,502 | A | 11/1998 | Van Vlasselaer |
| 6,071,422 | A | 6/2000 | Hlavinka et al. |
| 6,277,060 | B1 | 8/2001 | Neumann |
| 6,280,375 | B1 | 8/2001 | Meisberger et al. |
| 6,416,456 | B2 | 7/2002 | Zanella et al. |
| 6,497,674 | B1 | 12/2002 | Steele et al. |
| 7,297,272 | B2 | 11/2007 | Min et al. |
| 7,531,133 | B2 | 5/2009 | Hole |
| 2003/0026024 | A1 | 2/2003 | Igarashi |
| 2003/0026855 | A1 | 2/2003 | Kameneva et al. |
| 2003/0036518 | A1 | 2/2003 | Samain et al. |
| 2004/0102732 | A1 | 5/2004 | Naghavi et al. |
| 2005/0087122 | A1 | 4/2005 | Ismagliov et al. |
| 2006/0003439 | A1 | 1/2006 | Ismagilov et al. |
| 2006/0240964 | A1 | 10/2006 | Lolachi et al. |
| 2006/0280798 | A1 | 12/2006 | Ensoli |
| 2007/0026024 | A1 | 2/2007 | Drees |
| 2007/0258888 | A1 | 11/2007 | Feldmann |
| 2009/0088679 | A1 | 4/2009 | Wood et al. |
| 2011/0201986 | A1 | 8/2011 | Howell et al. |
| 2011/0224645 | A1 | 9/2011 | Winqvist et al. |
| 2012/0077662 | A1 | 3/2012 | Ostafin et al. |
| 2012/0164231 | A1 | 6/2012 | Ostafin et al. |
| 2014/0008301 | A1 | 1/2014 | Ostafin et al. |

FOREIGN PATENT DOCUMENTS

| | | |
|---|---|---|
| CN | 101322029 | 12/2008 |
| EP | 0416575 | 3/1991 |
| WO | 95/28915 | 11/1995 |
| WO | 99/02269 | 1/1999 |
| WO | 2005/097208 | 10/2005 |
| WO | 2006/115938 | 11/2006 |
| WO | 2008/107167 | 9/2008 |
| WO | 2011/025755 | 3/2011 |
| WO | 2011/025756 | 3/2011 |
| WO | 2014/008490 | 1/2014 |

OTHER PUBLICATIONS

Baran, et al., "Detection of Cancer Cells in the Blood by FACS Sorting of CD45-Cells", Int. J. Mol. Med., vol. 1, No. 3, 1998, 573-581.

Beltinger, et al., "A Simple Combined Microdissection and Aspiration Device for the Rapid Procurement of Single Cells from Clinical Peripheral Blood Smears", Mol. Path., vol. 51, No. 4, 1998, 233-236.

Brandt, et al., "Two-Layer Buoyant Density Centrifugation Gradient for Enrichment of Prostate-Derived Cells and Cell Clusters from Peripheral Blood", Clinical Chemistry, vol. 42, No. 11, 1996, 1881-1882.

Brugger, et al., "Mobilization of Tumor Cells and Hematopoietic Progenitor Cells Into Peripheral Blook of Patients With Solid Tumors", Blood, vol. 83, No. 3, 1994, 636-640.

Buckner, et al., "Leukapheresis by Continuous Flow Centrifugation (CFC) in Patients with Chronic Myelocytic Leukemia (CML)", Blood, vol. 33, 1969, 353-369.

Campana, et al., "Detection of Minimal Residual Disease in Acute Leukemia: Methodologic Advances and Clinical Significance", Blood, vol. 85, No. 6, 1995, 1416-1434.

Chang, "Blood Substitutes Based on Nanobiotechnology", Trends in Biotechnology, vol. 24, No. 8, 2006, 372-377.

Denis, et al., "Detection of Disseminated Tumor Cells in Peripheral Blood of Colorectal Cancer Patients", Int J Cancer, vol. 74, No. 5, 1998, 540-544.

Glaves, et al., "Haemotogenous Dissemination of Cells from Human Renal Adenocarcinomas", Br J Cancer, vol. 57, 1988, 32-35.

Harlozinska, et al., "Density Distribution, Cytomorphologic Features and Immunologic Characteristics of Ovarian and Endometrial Clear Cell Carcinomas", Acta Cytologica, vol. 34, No. 5, 1990, 657-663.

Henkel-Hanke, et al., "Artificial Oxygen Carriers: A Current Review", AANA Journal, vol. 75, No. 3, 2007, 205-211.

Hester, et al., "Principles of Blood Separation and Component Extraction in a Disposable Continuous-Flow Single-Stage Channel", Blood, vol. 54, No. 1, 1979, 254-268.

Hill, "Oxygen Therapeutics—Current Concepts", Canadian Journal of Anaesthesia, vol. 48, No. 4, 2001, S32-S40.

Jahr, "Blood Substitutes as Pharmacotherapies in Clinical Practice", Curr Opin Anaesthesiology, vol. 20, No. 4, 2007, 325-330.

Judson, et al., "Closed Continuous-Flow Centrifuge", Nature vol. 217, 1968, 816-818.

Kabalnov, et al., "Phospholipids as Emulsion Stabilizers. 1. Interfacial Tensions", Langmuir, vol. 11, No. 8, 1995, 2966-2974.

Karczewski, et al., "The Efficiency of an Autotransfusion System for Tumor Cell Removal from Blood Salvaged During Cancer Surgery", Anesth Analg, vol. 78, No. 6, 1994, 1131-1135.

Keipert, "OxygentTM, a Perfluorochemical-Based Oxygen Therapeutic for Surgical Patients", Blood Substitutes, Chapter 28, 2006, 312-323.

Kim, et al., "Artificial Oxygen Carriers as Red Blood Cell Substitutes: a Selected Review and Current Status", Artificial Organs, vol. 28, No. 9, 2004, 813-828.

Klein, et al., "Transperitoneal Oxygenation with Fluorocarbons", Anesthesia and Analgesia, vol. 65, No. 7, 1986, 734-738.

Koch, et al., "Duration of Red-Cell Storage and Complications after Cardiac Surgery", N Engl J Med, vol. 358, 2008, 1229-1239.

Ness, "Oxygen Therapeutics—Pursuit of an Alternative to the Donor Red Blood Cell", Arch Pathol Lab Med, vol. 131, No. 5, 2007, 734-741.

Ng, et al., "Buoyant Density of EMT6 Fibrosarcoma Cells", Cell Biophysics, vol. 2, No. 2, 1980, 153-163.

Racila, et al., "Detection and Characterization of Carcinoma Cells in the Blood", Proc Natl Acad Sci, vol. 95, No. 8, 1998, 4589-4594.

Sabile, "Efficiency of Ber-EP4 Antibody for Isolating Circulating Epithelial Tumor Cells Before TR-PCR Detection", Am J Clin Pathol, vol. 112, No. 2, 1999, 171-178.

Schmidt, "Calcium Phosphate Based Nanoshell for use in Biomedical Applications", University of Notre Dame Electronic Theses & Disertations, 2006, 1-347.

Suarez-Quian, "Laser Capture Microdissection of Single Cells from Complex Tissues", Biotechniques, vol. 26, No. 2, 1999, 328-335.

Thomas, et al., "Purification of Hematopoietic Stem Cells for Further Biological Study", Methods, vol. 17, No. 3, 1999, 202-218.

SYNTHESIS OF OXYGEN CARRYING, TURBULENCE RESISTANT, HIGH DENSITY SUBMICRON PARTICULATES

CROSS REFERENCE TO RELATED APPLICATIONS

This application is a Continuation-In-Part application of U.S. application Ser. No. 13/322,757, filed on Nov. 28, 2011, which is the National Stage of International Application No. PCT/US10/46417, filed Aug. 24, 2010, which claims the benefit of U.S. Provisional Application No. 61/236,810, filed on Aug. 25, 2009. The specification and claims of each is herein incorporated by reference.

FIELD OF THE INVENTION

The present invention relates to encapsulated active substances, such as perfluorocarbon, hemoglobin and polyhemoglobin, that are used as retrievable artificial oxygen carriers and/or retrievable carriers of therapeutic and diagnostic reagents in the blood or other liquids.

BACKGROUND OF THE INVENTION

In the field of medicine particulate carriers have been used to deliver medicines to the body and to serve as artificial oxygen carriers (AOC) in artificial blood products. Artificial blood is a product made to act as a substitute for red blood cells which transport oxygen and carbon dioxide throughout the body. However, the function of real blood is complicated, and the development of artificial blood has generally focused on meeting only a specific function, gas exchange—oxygen and carbon dioxide.

In contrast whole blood serves many different functions that has been difficult to duplicate by an AOC. Artificial blood mixable with autologous blood can support patients during surgery and support transfusion services in emerging countries with limited healthcare, blood donations and storage facilities, or high risk of exposure to disease since screening procedures are too expensive. A blood substitute, which is not dependent upon cross matching and blood-typing would mean no delay in blood availability, and could mean the difference between life and death of patients.

Blood donations are in short supply. Another motivation for developing improved AOC is that despite significant advances in donated blood screening there are still concerns over the limited shelf life which is 42 days at 2°-6° C.

Despite significant advances in donated blood screening and storage, concerns about the supply, cost and safety of donated stored blood remain. When testing blood for dangerous pathogens therein there is currently no practical way to test for emerging diseases such as Cruetzfeld-Jacob disease, smallpox and SARS. According to a 2000 NIH study, 10-15 million units of blood are annually transfused throughout the globe without testing for HIV and other diseases. This is particularly true for areas with high HIV-infected population such as South Africa where the percentage of people infected with HIV can be as high as 40 percent. A recent report (Koch C G, Li L, Sessler D I et al., Duration of Red-Cell Storage and Complications after Cardiac Surgery, New Eng. J. of Med. 2008; 358:1229-1239) details ill effects associated with using stored blood for open heart surgery and highlights the urgency to find artificial oxygen carriers (AOC) functioning as artificial blood as an alternative to the donated blood supply.

Chemically and biologically inert, emulsified, sterilized PFCs are stable in storage at low temperatures 2-5° C. for over a year. Further, PFCs are relatively inexpensive to produce and can be made devoid of any biological materials eliminating the possibility of spreading an infectious disease via a blood transfusion. Because they are not soluble in water they must be combined with emulsifiers able to suspend tiny droplets of PFC in the blood. In vivo the perfluorocarbon is ultimately expelled via the lungs after digestion of the emulsifier by the macrophage/monocyte system. In addition, PFCs are biologically inert materials that can dissolve about fifty times more oxygen than blood plasma but less oxygen than red blood cells. For instance, a mixture consisting of 70% blood and 30% perfluorocarbon by volume can provide the needed 5 ml of oxygen per 100 ml of blood if the partial pressure of oxygen in the lungs can be increased to 120 mm Hg by having the patient breath air with an oxygen partial pressure of approximately 180 mm Hg.

In contrast to the above described promising features for PFC based AOCs, use of such PFC-based AOCs has resulted in flu-like symptoms, a need for higher than normal oxygen pressure, problems such as emulsifier toxicity, formation of oxygen free radicals, long term retention of the AOCs in the tissue, damage to lung tissues, a decrease in platelet count, and problems related to loss of nitrous oxide (NO) from circulation in the blood. The loss of NO is also a problem with hemoglobin based AOCs. In addition, recent phase III trials for Oxygent (Alliance Pharmaceutical Corporation, San Diego, Calif.) which uses a stable perfluorooctyl bromide/perfluorodecyl bromide egg yolk phospholipid emulsion and has 4-5 times greater oxygen carrying capacity than Fluosol-DA-20 (Green Cross, Japan) have shown an increased incidence of stroke in treated patients compared to controls, and so trials of Oxygent have been halted.

PFCs dissolve more oxygen than water, but still less than normal blood. To supply the needed amount of oxygen in circulation, patients may require supplemental oxygen. Highly hydrophobic PFC requires emulsifiers to stabilize the droplet in blood. These emulsifiers interact with proteins and emulsifiers found in blood leading to instability. As a result, large quantities of PFC in circulation cannot be tolerated. Small amounts of PFC escape from the blood into the lungs where it is vaporized and breathed out. Large amounts of PFC and emulsifier can have a negative effect on lung function.

Crosslinked, polymerized or encapsulated hemoglobin based AOC are late-corners compared with PFC based AOCs described in previous paragraphs, and are attracting increasing attention because their oxygen delivery characteristics are similar to that of the red blood cells (hereinafter referred to as RBC). Some hemoglobin based AOCs are Hemolink, Hemosol, Optso and Hemospan, Polyheme (Northfield, USA), and Hemopure (Biopure Corp, USA). Some of these are at an advanced stage of development and have passed Phase III trials in Africa and Europe. However, there is a potential to transmit diseases from the animals from which the Hb was obtained and purified, and high production costs have slowed advances. Whether or not other side effects such as iron overload from localized enzymatic digestion in liver will emerge with these Hb based AOCs is still unknown.

Polymeric hemoglobins (pHb) bind $O_2$ and $CO_2$, with a binding mechanism much like that of red blood cells (RBC), but even a small quantity of unpolymerized Hb left in the circulation can become very toxic. As an AOC, a large amount of pHb needs to be injected into a person. Premature breakdown can increase the risk of toxicity, and such a large amount can overtax the body's natural removal processes. Polymerized Hb remains costly. Animal sources of Hb run the risk of transferring, among other things prion-based diseases. Recombinant Hb is a promising approach. It requires high quality separation and purification procedures, that add to the cost.

While both pHb and PFCs based AOC products deliver oxygen in significant quantities to cells and tissue, their side effects, such as nitric oxide related vasoconstriction, stroke, cardiac arrest, flu-like symptoms and long term chemical toxicity, have forced the termination of all the clinical trials in the U.S. An all-out effort to reduce the toxicity of relatively large quantity of AOC injected into a body by metabolic decompositions has failed.

The list of desirable features for safe artificial blood products is long and includes: adequate oxygen uptake in the lungs and delivery to the tissues, corresponding release of oxygen and removal of carbon dioxide from the tissues; wide applicability (i.e., no need for cross-matching of blood type of compatibility testing); free of side effects; non-toxic to the whole organism; reasonable circulation times; non-toxic and excretable without causing harm; no scavenging of nitrous oxide NO from the blood; non-immunogenicity; easily sterilizable to ensure absence of pathogens such as viruses; no interference with ordinary blood components; stable at room temperature and cheap to manufacture in large quantities; long shelf life and immediate full capacity oxygen transport when implemented.

Thus, in view of the many problems experienced with artificial blood products and particulate carriers intended for the controlled delivery of biologically active substances within the body, there is a need in the for improved AOC and particulate carriers that have one or more of the following characteristics: (a) do not break down unexpectedly and allow accidental release of active medicinal substances that may be toxic in unregulated doses in the body, (b) provide adequate oxygen uptake in the lungs and delivery to the tissues and corresponding removal of carbon dioxide from the tissues, (c) non-toxicity to the body, (d) does not scavenge nitrous oxide from the blood, (e) cheap to manufacture, (f) stable at room and low temperatures, (g) long shelf life, (h) free of side effects, (i) does not interfere with ordinary blood components, (j) has wide applicability so there is no need for cross-matching of blood type or compatibility testing, (k) are chemically and biologically inert so they are devoid of biological materials eliminating the possibility of spreading an infectious disease via a blood transfusion, (l) perfluorocarbon-based AOCs that do not have the problems previously experienced in the prior art, and (m) do not have to be tested for diseases.

SUMMARY OF THE INVENTION

One embodiment of the present invention provides for a particulate artificial oxygen carrier for use as a blood substitute, the particulate artificial oxygen carrier comprising a PFC material that can carry oxygen and carbon dioxide alike blood. The PFC material is emulsified to form a core of a carrier nanoparticle with an amphiphile emulsifier surrounding the PFC material. A first rigid inorganic shell is formed around the core of the carrier nanoparticle. A layer on the outside of the first rigid inorganic shell of each carrier nanoparticle is formed of a Hemoglobin embedded in a matrix of polylysine where the matrix of polylysine is bound to the first rigid inorganic shell wherein the Hemoglobin can transport oxygen and carbon dioxide alike blood. The second rigid inorganic shell around the polylysine/Hemoglobin layer is formed on the outside of the first rigid inorganic shell. The particulate artificial oxygen carrier has a higher density than any components of blood, and wherein the first rigid inorganic shell and the second rigid inorganic shell permit the particulate artificial oxygen carrier to be continuously circulated in a person's blood in a closed loop circulation system without releasing the PFC material inside the first rigid inorganic shell and the Hemoglobin embedded in the matrix of polylysine into the blood. The first rigid inorganic shell and or the second rigid inorganic shell may be calcium phosphate. The amphiphile emulsifier is phosphatidic acid, phosphatidylcholine or a combination thereof. For example the amphiphile emulsifier is lethicin or DOPA. The Hemoglobin can be a monomer or a polymer of monomers forming an aggregate in the size of about 2-10 or even larger. The Hemoglobin aggregate is not disulfide bonded or chemically crosslinked to itself or another chemical entity as the hemoglobin or Hemoglobin aggregate is electrostatically embedded in the polylysine matrix for example the Hemoglobin may diffuse within the polylysine matrix. In a further embodiment the particulate artificial oxygen carrier comprises a layer of carboxyethylphosphonic acid between the first rigid shell and the matrix of polylysine layer, the carboxyethylphosphonic acid forming a bond with the calcium phosphate to stop further growth of the first rigid inorganic shell.

According to another embodiment of the present invention is a method for making a particulate artificial oxygen carrier for use in place of blood in a person, the method comprising the steps of emulsifying a PFC material that can carry oxygen and carbon dioxide alike blood with an amphiphile emulsifier. The emulsified PFC material is formed into a core of a carrier nanoparticle. The core of the carrier nanoparticle is coated with a calcium phosphate layer to form a first rigid inorganic shell around the core of the carrier nanoparticle, the first rigid inorganic shell being permeable to oxygen and carbon dioxide. A layer is formed on the outside of the first rigid inorganic shell of the carrier nanoparticle, the layer being formed of a Hemoglobin embedded in a matrix of polylysine where the matrix of polylysine is indirectly bound to the first rigid inorganic shell wherein the Hemoglobin can transport oxygen and carbon dioxide alike. The polylysine/Hemoglobin layer is coated with calcium phosphate to form a second rigid inorganic shell on the outside of the first rigid inorganic shell wherein the particulate artificial oxygen carrier has a higher density than any components of blood, and wherein the first rigid inorganic shell and the second rigid inorganic shell permit the particulate artificial oxygen carrier to be continuously circulated in a person's blood in a closed loop circulation system without releasing the PFC material inside the first rigid inorganic shell and the Hemoglobin embedded in the matrix of polylysine into the blood. The method further comprises the step of coating the first rigid inorganic shell with a molecular monolayer to stop the growth of the first rigid inorganic shell and or coating the second rigid inorganic shell with a molecular monolayer to stop the growth of the second rigid inorganic shell. The amphiphile emulsifier may be selected from a phosphatidic acid, a phosphatidylcholine or a combination thereof. The Hemoglobin may be a monomer or a Hemoglobin aggregate formed of 2-10 Hemoglobin monomers. The Hemoglobin or the Hemoglobin aggregate is not disulfide bonded or chemically crosslinked to itself or another chemical entity. The Hemoglobin or Hemoglobin aggregate can diffuse within the polylysine matrix.

DESCRIPTION OF THE DRAWING

The invention will be better understood upon reading the following Detailed Description in conjunction with the drawing in which.

DETAILED DESCRIPTION

Figures 1A, 1B:
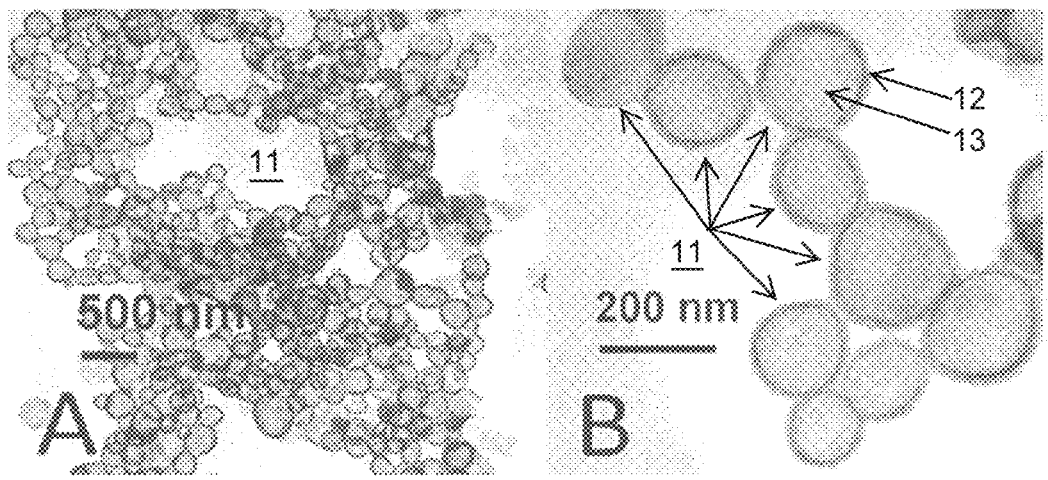
FIGS. 1A-B is a transmission electron microscope images of a plurality of submicron sized blood substitutes optimized for use with the described invention.

One or more embodiments of the present invention have one or more of the following features: (1) a particulate AOC made from a unique combination of organic and inorganic components whose physical and chemical properties permit functioning as an AOC while being retrievable from whole blood using density-gradient continuous flow centrifugation, (2) an AOC whose synthesis may be carried out by either a batch method or continuous method, and (3) a specialized centrifugal rotor based on density gradient separation to accomplish the task of removal from blood or other biofluids. In one embodiment of the present invention, the AOC is retrieved from a patients system as soon as its medical purpose is accomplished in order to alleviate the physiological stress on already compromised patients.

The particulate artificial oxygen carrier of one embodiment is designed to be continually circulated in a closed loop fluid circulation system, is not subject to turbulent breakup, chemical decomposition, or accumulation of debris, and does not release its payload but is capable of exchange of small ions and gases, and which can be retrieved at any time desired using continuous flow separation employing density-gradient centrifugation, which may be supplemented with magnetic fields, affinity filtration or other methods, without suffering damage, or inflicting damage on other materials that may already be present in the flowing fluid.

As used herein AOC includes single shell and double shell embodiments of the oxygen carrying particle. Shell as used herein describes a rigid layer. Other features of the particulates used in the AOC of an embodiment of the present invention may include one or more of the following: (1) particulates made in sizes large enough to remain in circulation (i.e. greater than 50 nm and smaller than 2 μm), (2) particulates designed to resist mechanical breakup in turbulent flow conditions, (3) particulates designed to avoid adherence to blood corpuscles and blood proteins, (4) particulates which do not adversely affect the normal physiological function of existing blood components, (5) particulates resistant to phagocytosis, (6) particulates with low toxicity, (7) particles which avoid blood vessel occlusion, (8) particulates which can be tailored to exchange gases with the environment similarly to normal red blood cells and (9) particulates capable of carrying drugs, optical, X-ray, radiographic or MRI imaging tracers, magnets or mobile chemical sensors.

Existing AOC products may meet one or more of the above listed criteria for in vivo use as an AOC, but they are not designed for continuous retrievability from the bloodstream using centrifugation as can be done with one or more embodiments of the present invention.

To help achieve the above goals for an AOC one embodiment of the present invention relates to the synthesis of a carrier particle designed to be continually circulated in a closed loop fluid circulation system, such a blood stream of a person, that is not subject to turbulent breakup, chemical decomposition, accumulation of debris, does not release its payload but is capable of exchange of small ions and gases, and which can be retrieved at any desired time. To remove the carrier particles from the blood one or more of the following continuous flow separation methods may be used: (a) centrifugation, (b) magnetic fields, and/or (c) affinity filtration without suffering damage or inflicting damage on other materials that may already be present in the flowing fluid. It is contemplated that AOCs be removed from the bloodstream as soon as possible after they have performed their function, but prior to simultaneous degradation of the AOCs and development of side effects.

In an embodiment of the present invention, retrievable AOCs are synthesized having both single and double shells to create micron or submicron sized particulates/particles that encapsulate gas-absorbing substances such as a PFC or a pHb. Very briefly, one synthesis process for making coated PFC based carrier particles provides: (a) the formation of a stable, turbulence resistant PFC emulsion, (b) layer by layer synthesis of poly-hemoglobin, and (c) forming one or two shells to protect the carrier particle. These particles may also be used as carriers for therapeutic and diagnostic reagents in the blood or in other liquids. The encapsulation is accomplished using a batch or continuous flow synthetic method. The shells help resist mechanical breakup in turbulent flow conditions, avoid adherence to blood corpuscles, they do not adversely affect the normal physiological function of existing blood components, they are resistant to phagocytosis, have low toxicity, and they avoid blood vessel occlusion. The novel shell prevents the release of the PFC inside the AOC but allows the exchange of gases and small ions between the blood and the encapsulated PFC.

To produce a stable, turbulence resistant retrievable PFC nanoemulsion for the single shell AOC there are two methods. The first method is to use a complex mixture of several surfactants, an oil mediator and other additives or specially designed fluorinated alkyl tail phosphatidylcholine-type surfactants is used. The second method uses ionic hydrocarbon-based surfactants such as phosphatidic acids to stabilize nanoemulsions and is the preferred method that is described in detail below.

To meet the criteria for retrievability of the above described AOC particles of the present invention from blood during their use, the particulate material must be submicron sized (50 nm-700 nm) hollow particles filled with a high density perfluorocarbon liquid. These particles are surrounded by one or two rigid reinforcing shells. The exterior surface of these particulate shells are coated with molecules containing exposed functional groups (COOH, $NH_2$, SH etc.) convenient for the crosslinking of either more than one particle, or proteins like antibodies, cell receptor targets, polyhemoglobin, hemoglobin etc.

More particularly, as a first way to synthesize such submicron sized single shell coated PFC particles as AOCs, perfluorocarbons such as perfluoroctyl bromide or perfluorodecalin are emulsified at room temperature with 1,2-dioleoyl-sn-glycero-3-phosphate (DOPA) or an equivalent lipid with a density higher than that of red blood cells. Emulsifiers other than DOPA are described in the Detailed Description. The perfluorocarbon and emulsifiers are extruded multiple times through an extrusion membrane using an extruder at temperatures ranging from 20-90 C. The submicron structures produced by the extrusion process are then coated with a 5-20 nm-thick shell of calcium phosphate, and these particles are overcoated with a slight excess of carboxyethylphosphonic acid (CEPA) which carboxylates the particle surface, stops further growth and inhibits self-aggregation of the particles at physiological pH. The materials are concentrated centrifugally, and the final product is dialyzed against a phosphate buffered saline and sterilized by autoclaving without any damage to the coated particles.

A variant way to produce the single shell coated emulsion particles is to feed the phosphate-buffered PFC or Hb emulsions in a well-mixed flow through a reactor containing a fixed concentration of sterile calcium chloride solution at an appropriate pH. While in the reactor the calcium and phosphate in the mixture nucleate a reinforcing layer around the emulsion particles, and the suspension will then enter a rotating basket or finishing reactor in which a small amount of CEPA (enough to cover the available surface area of the particles in that volume) is added, and the resulting mixture is concentrated and collected.

The single shell coated emulsion particles or AOC have a higher density than other components of blood such as red blood cells, white blood cells and plasma. Accordingly, centrifugal forces may be utilized to separate the particles from other blood components, but density gradient is used rather than sedimentation velocity. In sedimentation separation red blood cells are the furthest moving particles in a centrifugal field, but with separation of the AOC particles of the present method according to one embodiment, an AOC is the furthest moving particles in the centrifugal field. With the AOC being the furthest moving particles in a centrifugal field they may be separated from all other blood components.

The single shell coated PFC particles of the present invention used as artificial oxygen carriers are typically added to the blood of a person and they circulate with the blood stream to exchange oxygen and carbon dioxide in the same manner as blood.

Figure 5:
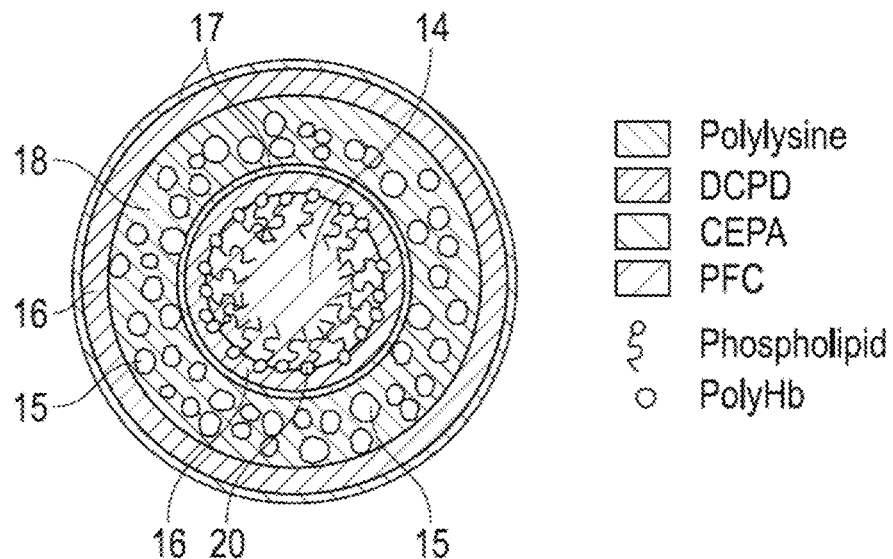
FIG. 5 is an illustration of a DCOC according to one embodiment of the present invention.

Referring now to FIG. 5, a second embodiment of the present invention is a dual cored oxygen carrier (DCOC) that is synthesized having a double shell of an inorganic such as CaP to create micron or submicron sized particulates that encapsulate active substances such as a PFC and/or pHb surrounded by an emulsifier. Very briefly, the synthesis process for making coated PFC based carrier particles requires: (a) the formation of a stable, turbulence resistant PFC emulsion (i.e. PFC+amphiphile emulsifier wherein the emulsifier may be for example any one or more of the following selected from lecithin, phosphatidic acids, phosphatidylcholine silicates (i.e. with an SiO3 instead of a PO3 attached to a one or more hydrocarbon chains), synthetic polymers with a hydrophobic and hydrophilic end that act like phospholipids and possibly transition metal oxide terminated lipids), (b) inorganic shell adjacent to the emulsifier layer; (c) CEPA separating the rigid inorganic shell from the pHb layer and (d) layer by layer synthesis of pHb and poly-lysine, and (e) forming a rigid inorganic shell around the pHb/poly-lysine to protect the carrier particle.

More specifically, the emulsifier (for example DOPA, an example of a phosphatidic acid) and a PFC are mixed and extruded through porous membranes of a selected diameter to form a PFC emulsion of small particles having submicron size. The resultant emulsion is suspended in a phosphate buffer solution and a $CaCl_2$ solution is slowly added to form a thin layer of DCPD on the emulsion particles to stabilize them. Next, the DCPD surface of the first shell is carboxylated with carboxyethylphosphonic acid (CEPA) to create a layer that prevents aggregation/growth of the emulsion particles. CEPA has a phosphate group and carboxyl group on either end. In the middle are 2 carbons. The phosphate group links ionically to the calcium phosphate shell. The other end points outward. No bonds are cleaved.

The thickness of the second shell may be controlled by the duration of DCPD shell formation. Unreacted reagents are then removed by dialysis or centrifugal membrane filtration. The density of the finished emulsion particles is greater than the density of blood and may be separate by centrifugation. The DCOC particles have an oxygen dissociation curve similar to that of normal blood and have a sufficiently fast permeability to exchange gases in the lungs and tissue, that is they deliver oxygen and remove carbon dioxide alike normal blood. In addition, the DCOC particles are strong enough to withstand normal turbulence during blood circulation and, having two different kinds of oxygen carriers, PFC and pHb, the toxicity of DCOC is expected smaller than of AOCs having a single component.

AOCs in the blood have a higher density than the blood and are separated therefrom by continuous flow density gradient centrifugation that utilizes the higher density of the AOC particles to accomplish their separation. Affinity filtration may also be used to separate the AOC nano or sub-nano size particles from the blood.

In addition, paramagnetic materials may be added to the higher density PFC in each nanoparticle, and the magnetic susceptibility is used for the retrieval of the polymerized hemoglobin. The flowing liquid containing paramagnetic and diamagnetic materials (the natural blood component) must be exposed to a magnetic field during the centrifugal separation so that they will deviate in the direction of the flow of particles with paramagnetic materials away from the diamagnetic particles, thus making it possible to separate and collect both types of particles.

Most uncoated nanoemulsion particles have many drawbacks such as being too fragile and the uncoated nanoemulsion particle unexpectedly allow accidental release of active medicinal substances that may be toxic in unregulated doses in the body. The coated AOC nanoemulsion particles described herein do not suffer from this deficiency. To meet the criteria for artificial oxygen carriers (AOC) that can be temporarily substituted for blood, and for the retrievability of the AOCs from blood, the AOCs described herein are particulates having shells in accordance with embodiments of the present invention. According to one embodiment the AOC shells are submicron sized (50-1000 nm) hollow particles around a high density perfluorocarbon (PFC) emulsified nanoparticle. The reinforcing shell is rigid and consists of a combination of lipids and inorganic materials like calcium phosphate, silicate, or biocompatible organic polymers such as, but not exclusively: polycaprolactone, polylactic acid, polyglycolic acid, polyethylene oxide, chitosan or chondroitin. According to one embodiment the shell does not include crosslinks such as disulphide. The AOCs nanoemulsion core particles are denser than blood and the higher density is used to retrieve them from blood using a special centrifuge.

FIG. 1 shows typical electron microscope pictures of the AOC particles 11. The shells 12 of these novel AOC particles 11 may be coated with molecules containing exposed functional groups (COON, NH$_2$, SH etc.) convenient for the crosslinking of either more than one particle, or proteins like antibodies, cell receptor targets, polyhemoglobin, hemoglobin etc. Outer ring or shell 12 is a rigid inorganic shell such as gas permeant calcium phosphate or polymer coating, while the interior is an oxygen carrying center containing an Hb 13 and/or a PFC 13 emulsion to form the entire nanoparticle.

Producing PFC emulsions in water is challenging due to the limited solubility of hydrocarbon-based emulsifiers in the PFC, a fact which is also linked to their instability in biological media, at elevated temperatures, and during sterilization. To emulsify the PFC, 1,2-dioleoyl-sn-glycero-3-phosphate (DOPA) or similar phosphatidic acids of varying chain length and structure, lecithin and similar phosphatidylcholines of varying chain length and structure, mixture of these, and mixtures of these with other additives used in the field by others including single chain surfactants, triglycerides, and partially fluorinated compounds are utilized.

To form nanoemulsions in water in high yield there are two main approaches: (a) to use a complex mixture of several surfactants, an oil mediator and other additives; or (b) to use a specially designed fluorinated alkyl tail phosphatidylcholine type surfactant. The latter adds to cost and complexity. Another approach is to use ionic hydrocarbon-based surfactants such as phosphatidic acids. These emulsifiers have not been used in the past to prepare PFC emulsions but present some advantages. The highly negatively charged head group of the emulsion particle is expected to increase the curvature of the formed emulsions, with the result favoring smaller, nanosized emulsions with greater stability at least under mild conditions.

To improve upon the emulsification process and achieve an increase in the per batch emulsion PFOB perfluoroctylbromide content lecithin is substituted for DOPA or other emulsifiers as the emulsifier in a 0.334 M phosphate buffer. The increase in emulsified nanoparticles may be from 5% to 70% but the optimal increase for AOC formation has been found to be about 40 vol. %. This figure chosen for convenience and stability of the AOC formation process. Higher concentration material could be used, but the resulting higher viscosities introduced problems with mixing and extrusion. In addition, the lecithin is significantly cheaper than using DOPA and the result is that the AOC and DCOC products are significantly cheaper. The optimum emulsion solution was found to have 0.25% lecithin with between 0.1% and 0.6% PFOB in water.

Many reported PFC nanoemulsions used in imaging, tissue oxygenation and as a therapeutic measure have short lifetimes and this leads to systemic and cellular side effects made worse when a large quantity or prolonged exposure time is needed. We show that negatively charged phosphate head groups of the nanoemulsion particles are easily mineralized with a layer of calcium phosphate, which are much more resiliently reinforced both mechanically as well as chemically. Such oxygen delivery particulates resistant to turbulent break up materials can be of use in microfluidic devices, in bacterial and mammalian cell culture systems, and in chemical reactors where adequate and efficient oxygenation is required, but where weaker emulsified PFCs supplemented with polyethylene glycol, cross-linked proteins, and other polymers have met with a limited success. Other than liquid PFC a gaseous form of perfluorocarbon could be made that is highly volatile and the synthesis carried out at a low temperature to avoid perfluorocarbon evaporation.

A preferred method of synthesis of the perfluorocarbon AOCs particles involves emulsification of perfluorocarbons such as perfluoroctyl bromide or perfluorodecalin or other suitable PFC at room temperature with 1,2-dioleoyl-sn-glycero-3-phosphate (DOPA) or equivalent lipid (Avanti Lipids), as described above, with density higher than that of red blood cells (RBC). For example, 100 ml batches of mixtures of perfluorocarbon and emulsifiers are extruded multiple times through a 300, 400, 500, 600 or 700 nm pore size polycarbonate extrusion membrane (Millipore) using a Thermobarrel LIPEX extruder (Northern Lipids) to create emulsified particles. The submicron sized emulsified particles are then coated with a 5-20 nm-thick layer of calcium phosphate 12 to form a shell of CaP layer, and mixed with a slight excess of carboxyethylphosphonic acid (CEPA) which carboxylates the particle surface of CaP, stops further growth of the CaP layer and inhibits self-aggregation of the particles at physiological pH. The materials are concentrated centrifugally to higher than 50 vol % and the final product is dialyzed against phosphate buffered saline using 100,000 MWCO Spectrapore dialysis tubing (Pierce) and sterilized by autoclaving without any damage to the particles. The concentrated nanoparticles are collected in a sterile reservoir. The osmolarity of the collected final AOC nanoparticle is measured and adjusted with sterile PBS if necessary. Other materials may be used to form the shell such as a silicate, or biocompatible organic polymers such as, polycaprolactone, polylactic acid, polyglyocolic acid, polyethylene oxide, chitosan or chondroitin.

In a variant embodiment, the synthesis of these materials involves slowly feeding prepared phosphate-buffered PFC or Hb emulsions in a well-mixed flow through a reactor containing a fixed concentration of sterile calcium chloride solution at an appropriate pH. During the residence time of the emulsions in the reactor, the calcium and phosphate in the mixture nucleate a reinforcing shell 12 around the emulsion particles 13, and the suspension will then enter a rotating basket/finishing reactor in which a small amount of CEPA 18 (enough to cover the available surface area of the particles in that volume) is added, and the resulting mixture concentrated, and collected in a sterile reservoir. The osmolarity of the collected final AOCs is measured and adjusted with sterile PBS if necessary. A reactor according to one embodiment is shown in and described with reference to FIG. 7. CEPA is preferred because one side matches the existing CaP coating and the other side is carboxylated which is typical for many biomedical materials and easy to crosslink things to via known chemistries. A bifunctional or trifunctional ligand can be used in lieu of CEPA because these molecules have one or two ligands designed to stick to the particle and one or two designed to stick out, or eventually be chemically cross linked to some other molecule which could be a polymer, protein, etc. For non AOC applications it could be antibodies for targeted delivery for example. CEPA's important secondary function is to increase the surface charge the particle so that the suspension of particles stays stable (all particles are mutually repulsive) during the next steps of adding poly lysine/hemoglobin/more DCPD. Without this, the core particles will precipitate as each new ingredients obscures the charge. As the charge dwindles the van der waals interactions between particles become uninhibited and aggregation can occur.

If a silicate were used instead a CEPA analogue would be a silicate group in place of the phosphate group. If a polymer coating were used as a shell instead of CaP an amine or a sulfur based material would be used to stick to the polymer shell, but still use a carboxyl group on the exterior of the shell so that the surface charge would be negative and make the particle stable and repel proteins.

More specifically, single shell AOCs 11 are made as follows. Shown diagramatically is the process of mineralization of nanoemulsion particles to make single shell AOC particles 11. The nanoemulsion particles 13 are made from a mixture of perfluorooctylbromide (PFOB) 21,1,2-dioleoyl-sn-glycero-phosphate (DOPA) and water, preferably by a stirring process that is described elsewhere in this Detailed Description with reference to FIG. 7, but other methods known in the art may be utilized.

Raw materials typically needed to make the single shell AOC particles 11 were obtained from the following sources. First there are: (a) reagent grade calcium chloride ($CaCl_2$), (b) phosphoric acid ($H_3PO_4$), (c) sodium chloride (NaCl), and (d) sodium hydroxide (NaOH) that were all obtained from Fisher Scientific in Pittsburgh, Pa. Other raw materials needed are (a) carboxyethylphosphonic acid (CEPA), (b) perfluorooctylbromide (PFOB) and (c) Dulbecco's Modified Eagle Media (DMEM) that were all obtained from Sigma-Aldrich in St. Louis, Mo. Still other raw materials needed are; (a) 1,2-dioleoyl-sn-glycero-phosphate (DOPA), and (b) 1-Palmitoyl-2-[12-[(7-nitro-2-1,3-benzoxadiazol-4-yeamino]dodecanoyl]-sn-Glycero-3-Phosphocholine (16:0-12:0 NBD PC) and similar lipids which were obtained as lyophilized powder from Avanti Polar Lipids in Alabaster, Ala. Then there are packed red blood cells (RBC) obtained from ARUP Laboratories in Salt Lake City, Utah. Finally, 18 M.OMEGA. deionized water was obtained from an E-Pure water filtration system in Millipore, Billerica, Mass.

A typical recipe for making the single shell AOC particles 11 is to mix 50 µl of PFOB with 5 ml of a 0.69 mM DOPA solution in water. When stirred at 1200 RPM at room temperature for 30 minutes such a mixture yielded a nanosized homogenous emulsion ranging around 350 nm in mean size with a relatively broad size dispersion. Refinement of the distribution and size reduction is accomplished by extruding the mixture through an appropriate pore-size (between 60 and 200 nm) polycarbonate extrusion membrane (Millipore, Billerica, Mass.) using a 10 ml Thermobarrel LIPEX extruder (Northern Lipids, Vancouver, Calif.). Industrial grade nitrogen gas was used to drive the fluid through the membrane at 800 PSI to achieve a flow rate of .about.0.2-1.0 ml/min. Membrane pore sizes were tested to determine the nanoemulsion sizes obtained in each case. Suspensions were allowed to rest about 1 hour after extrusion before proceeding to subsequent steps of coating the nanoemulsion particles.

In testing mineralized nanoemulsion samples were imaged with a JEOL 100-SX transmission electron microscope (JEOL, Tokyo, Japan) operating at 100 kV. One to two liters of shaken suspension were placed in the center of carbon coated 300-mesh copper grids with a Formvar support (Ted Pella, Redding, Calif.) and allowed to air dry. Images were captured on film and particle diameters were compared to those in calibrated TEM images. See FIG. 1.

Figure 3:
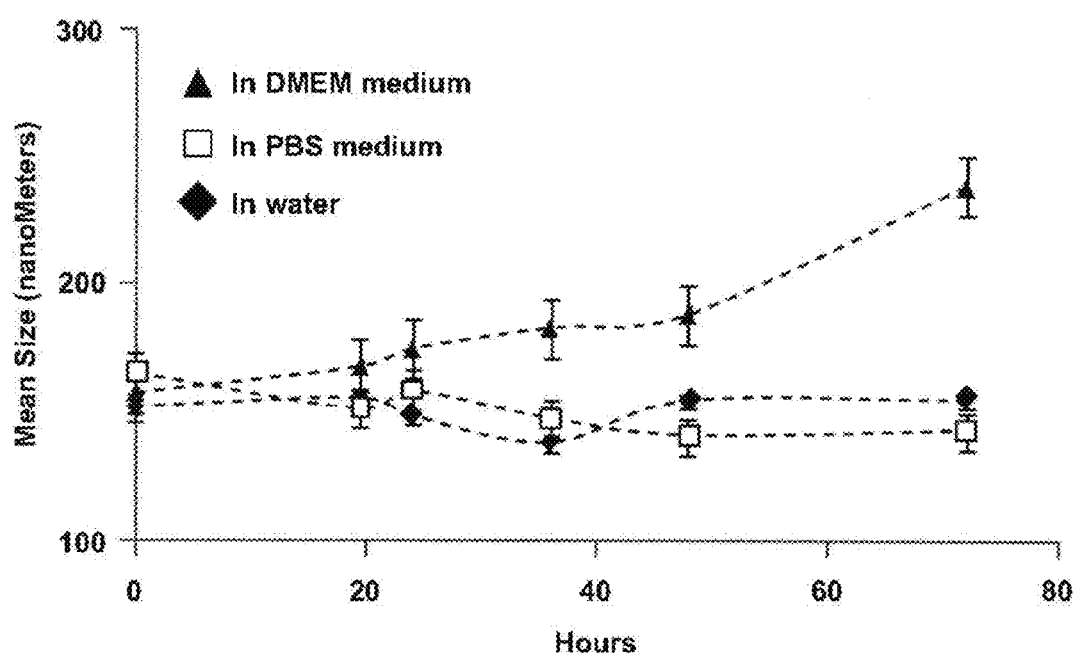
FIG. 3 shows the stability of the single shell AOC particles in different types of solutions over the course of a period of time.

The mean particle hydrodynamic diameter, polydispersity index (PDI) and percent polydispersity defined as (PDI)×100 of the product prepared at a suspension concentration of 20 nM were obtained at 20° C. using a Zetasizer Nano ZEN3600 (Malvern Instruments, Malvern, Worcestershire, UK). This instrument is capable of particle size measurements in the range 0.6 nm to 6 microns, and utilizes a configuration in which the scattered light is detected from the front of cuvette at an angle of 7 degree. This means that concentration of the sample is less critical for obtaining accurate size measurements than is the case for conventional light scattering instrument in which the signal is detected at 90.degree. The thickness of the shells was determined by subtracting the mean size distribution of particles from that of the initial nanoemulsion. The sizes of the nanoemulsion particles when in water, DMEM medium and PBS medium are shown in FIG. 3.

According to one example, perfluorooctylbromide (PFOB) nanoparticles has a surface of 1,2-dioleoyl-sn-glycero-phosphate (DOPA) surrounding a nanomulsion particle. The uncoated (non-mineralized) nanoemulsion particles have a negatively charged surface of $PO_3^-$ created by using phosphatidic acid to stabilize the nanoemulsion particles. Since the synthesis of nanoemulsion particles takes place under basic conditions, the surface charge density of the nanoemulsion is quite high with zeta potentials nearing −50 mV.

To coat the negatively charged nanoemulsions particles in a batch process, 600 µl of nanoemulsion suspension were mixed with 2:00 µl of 0.1 M phosphoric acid solution previously titrated to pH 7 with 0.1 M NaOH. The mixture was magnetically stirred at room temperature in a 100 ml beaker at a speed of .about.400 RPM. Next, 270 µl of 0.1 M NaOH were added to adjust the pH of this mixture to 9.5. Fifteen to thirty 10 µl aliquots of 0.1 M aqueous $CaCl_2$ solution were added at 30 minute intervals to the reaction vessel containing the nanoemulsion using two Tecan XP-3000 syringe pumps controlled by a LabVIEW version 6.0 program (National Instruments. Austin, Tex.) running on a personal computer. One hour after the last addition of 0.1M $CaCl_2$, 100 µl of 0.1 M CEPA solution (prepared at pH 7.0) were added to coat the particles and arrest further calcium phosphate deposition.

Figure 8:
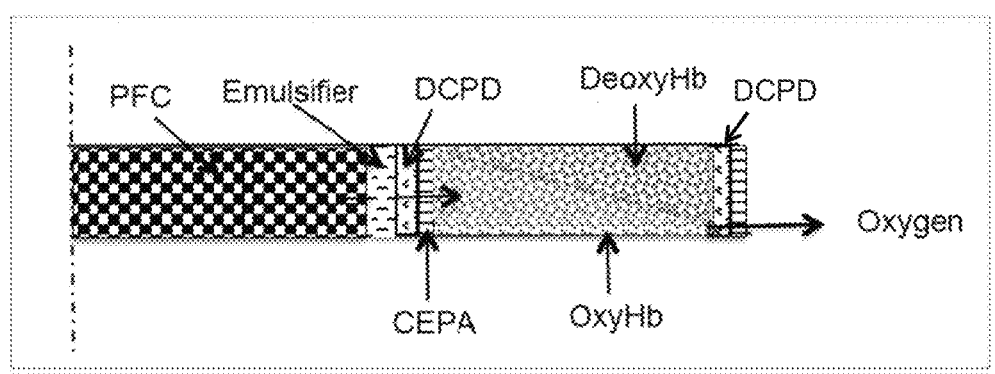
FIG. 8 is a schematic diagram of a cross sectional view of a DCOC particle.

In this process positively charged calcium ions from the phosphoric acid are attracted to the negatively charged $PO_3$ on the surface of the nanoemulsion particles (DOPA). The accumulation of calcium ions at the periphery of the nanoemulsion particles increases the local concentration past the stability point for calcium phosphate precipitation resulting in precipitation of calcium phosphate onto the nanoemulsion particles. This creates the first Calcium Phosphate (CaP) shell as shown in FIG. 5 and FIG. 8. Because the concentration of ions in the bulk solution is low, precipitation at the nanoemulsion/solvent interface is preferred. The dominant form of calcium phosphate produced in this manner is brushite. Other than a CaP shell other materials such as chitosan, chondroitin, and calcium carbonate may be utilized to create the shell, and/or a mixture of CaP and these materials and/or other minerals.

To concentrate the product created, as described in the previous paragraphs, 25 ml of mineralized nanoemulsions particles is placed in a 50 ml conical centrifugal tube (Fisher Scientific, Pittsburgh, Pa.) and centrifuged in a Sorval T20 Superspeed Centrifuge (ThermoFisher, Pittsburgh, Pa.) using a model SL250T rotor at 10,000 RPM for 1 hour, and the supernatant decanted. Usually 5 ml of concentrated product is harvested resulting in a suspension that contained approximately 10% of PFOB. The centrifuged samples were dialyzed using 100,000 MWCO Spectrapore dialysis tubing (Pierce, Rockford, Ill.) against 0.1 mM phosphate buffer at pH 7.0 to remove un-reacted and un-encapsulated materials.

This creates the basic CaP single shell AOC as shown in FIG. 1B. In a final step a coating 18 of CEPA is added over the CaP shell. One hour after the last addition of 0.1M $CaCl_2$ to create the CaP shell, 100 µl of 0.1 M CEPA solution (prepared at pH 7.0) is added to coat the particles with single molecular layer of CEPA and arrest further calcium phosphate deposition. The completed AOC nanoparticles are shown diagramatically in FIG. 1B.

Stability of the uncoated nanoemulsion particles and the mineralized CaP shell thereon forming particles 11 was evaluated at 37° C., under vigorous stirring, sonication and autoclave sterilization. For temperature studies, nanoemulsions and the corresponding mineralized particles were incubated at room temperature and 37° C. for 30 days. Every five days the mean sizes were determined using dynamic light scattering as described. For vigorous mixing an orbital shaker was used to apply shear force to the particles and mean particle sizes were measured daily. For sonication tests, a Branson cell homogenizer was used, and mean particle size was measured every 30 minutes. Finally samples were treated to one autoclave sterilization cycle at 121° C. for 30 minutes and it was determined that the coated particles were not destroyed.

The use of the nanoemulsion particles, single coated as described above with reference to FIG. 1 and was tested for their use as an AOC 11. See FIGS. 4(A-C). The slopes of the lines were adjusted to the concentration of hemoglobin used and the final rates were estimated to be 4.8, 14.5, and 15.2 sec.$^{-1}$ respectively. For RBC the equivalent constant is 4.1 sec.$^{-1}$.

Figure 4A:
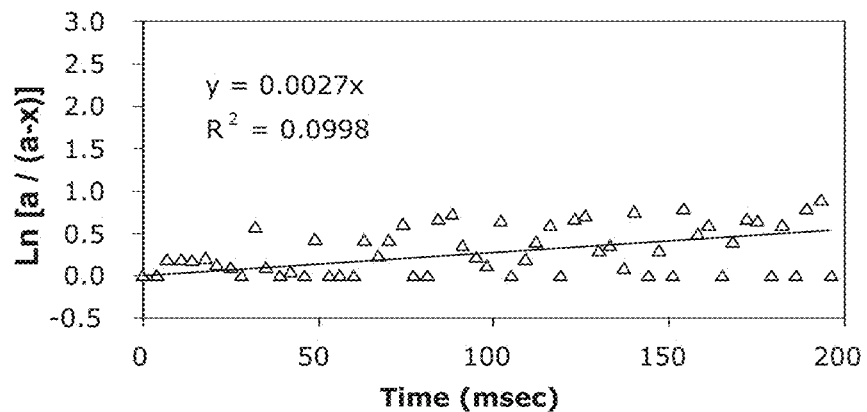
FIG. 4A-C illustrates three graphs showing the estimated rate of oxygenation of single shell AOC particles of one embodiment of the present invention for different concentrations of hemoglobin.
Figure 4B:
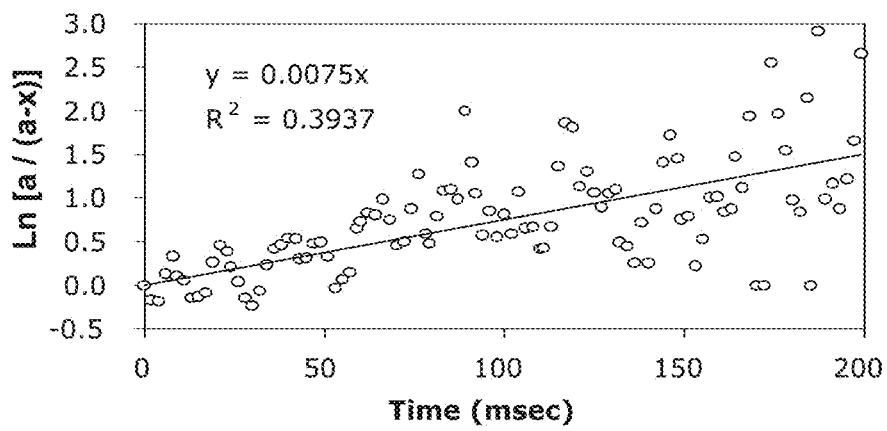
Figure 4C:
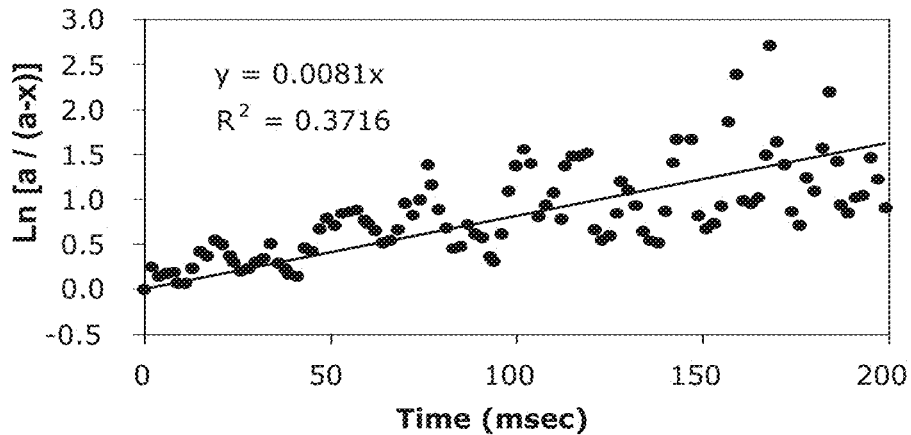

To get data to create the graphs in FIGS. 4(A-C) hemolysis of red blood cells (RBC) in the presence of the nanoemulsion particles was tested at room temperature by incubating 0.5 ml samples of RBC/plasma mixture at a 20% hematocrit with 0.5 ml emulsion and mineralized particles prepared in isotonic PBS. The micromoles released and % of hemoglobin released from the RBC was measured as a function of volume % of nanoemulsion or mineralized nanoemulsion particles from 0-8%. At each concentration of particles used, the amount of RBC hemolysis was spectrophotometrically determined in the supernatant of the mixture after 15 min of centrifugation at 3,000 RPM to remove cells and other debris, by assuming the molar absorptivity of hemoglobin at 575 nm to be 55,540 cm$^{-1}$ M$^1$.

Figure 2:
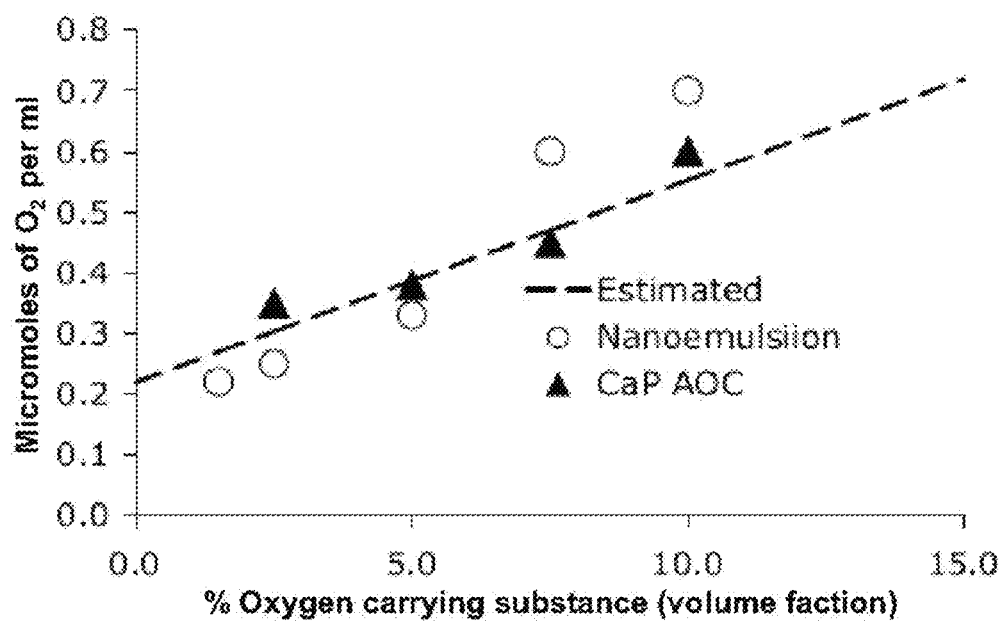
FIG. 2 is a graph showing the estimated oxygen content of varying concentrations of the PFC blood substitute emulsion (AOC) and the submicron size blood substitute showing equivalent oxygen carrying capacity per unit weight of oxygen carrying material.

To confirm the oxygen carrying capability of the single coated nanoemulsion particle AOCs, the amount of dissolved oxygen in water was measured. The linear dependence of the absorbance at 540 nm in response to the concentration of glucose was first confirmed at 37° C. in the presence of sufficient amount of oxygen, and then the limiting amount of oxygen concentration was estimated in the presence of sufficient amount of glucose. In practice, the calibration for the concentration of oxygen, 200 µl of refrigerated glucose assay solution (a mixture of o-dianisidine, glucose oxidase and peroxidase) were poured into a 10 ml centrifuge tube, covered with a septum and evacuated for 5 minutes using a rotary vacuum pump followed by purging with nitrogen gas for 5 minutes. The degassing and purging were repeated a second time and the centrifuge tube kept at 37° C. in a water bath. Ten (10) µl each of a similarly deoxygenated glucose solution containing 100 mg glucose/ml was mixed with 0, 25, 50, 75, 100, and 150 µl of the air equilibrated DI water at 37° C., and the mixtures were added to the deoxygenated glucose assay solution prepared in the above and allowed to react for 30 minutes at 37° C. Finally, 200 µl of 12 $NH_2SO_4$ was added to each sample to stop the reaction. The DI water was added to make the total volume 1.41 µl and the absorbance determined at 540 nm. The absorbance was plotted against the molar concentration of dissolved oxygen assuming that the air at 1 AP and 37° C., water contains 215.6 µmol/L of $O_2$. The experimentally determined oxygen content in the coated AOC suspension is a composite of oxygen content in water and in the perfluorocarbon. Quantitatively, $$CO_2\ total = CO_2\ PFC\ VPFC + CO_2\ water\ Vwater = CO_2\ PFC\ VPFC + CO_2\ water(1-VPFC) \quad \text{(Equation 1)}$$

where, $CO_2$ total is the total oxygen concentration of the sample, and $CO_2$ PFC and $CO_2$ water are the concentrations of oxygen in PFC and water at a given partial pressure of oxygen and temperature, and similarly V's are the volume fractions of PFC and water. If the oxygen solubility is known for each phase, $CO_2$ total can be estimated for a given volume fraction of PFC. The oxygen content of emulsified PFOB has an estimated $C_{SAT}$ of 3,640 µmol/L of 0.2 at 37° C. and at 1 AP. A suspension of uncoated and coated particles were concentrated to 10% v/v by centrifugation at 10,000 rpm for 1 hour. Using Equation (1) above and letting VPFC=0.1, the – concentration of oxygen in the air-equilibrated stock solution was determined to be 558.0. Two hundred (200)µl of product was serially diluted with PBS at pH 7.4 to prepare 5 different concentrations of suspensions ranging from 0 to 250 nM. To 200 µl of each air-saturated suspension at 37° C., 200 µl of a previously prepared deoxygenated glucose assay solution together with 1 µl of 100 mg/ml glucose solution were added. The reaction was allowed to proceed for 30 minutes at 37° C. and the absorption was measured at 540 nm in order to estimate the amount of oxygen present in the uncoated and coated products. See FIG. 2.

For these materials to be suitable as tissue oxygenators, the rate of oxygen uptake from the bloodstream has to be commensurate with oxygen offload rate from the blood in the tissue capillaries. For red blood cells the rates of oxygen uptake and release are determined at the point of 50% of the maximum change are reported as 0.4 and 1.1 sec, respectively, and the deoxygenation constant estimated as a pseudo-first order constant is 4.11.+−0.0.2 sec$^{-1}$. The rates of deoxygenation of the product was estimated indirectly from the rates of uptake of oxygen by deoxygenated hemoglobin (Hb) solution, since the latter rate is considerably faster than that of the former. Measurements of oxygen uptake by deoxygenated Hb were made using the Aminco stopped flow instrument with 30 ms mixing time. An Hb solution was prepared from freshly obtained blood cells and washed several times in saline. The red blood cells were collected centrifugally and hemolyzed with 10 times volume of cold DI water and membrane fragments were removed by centrifugation at 3,000 rpm for 20 minutes. The pH was adjusted to 7.0 and used without further purification. The concentration of Hb was approximately 0.5 mM. Deoxygenation of Hb was conducted by purging with nitrogen gas until the absorption peak of the solution at 585 nm became negligible. The concentrations of the PFOB-nanoemulsion and the particles were set at approximately 10 vol. % and their pH values were adjusted to 7.0. The increase of spectral absorption at 585 nm was observed over time at 25° C. after rapid mixing of the Hb with the nanoemulsion or the particles. An average of three successive stopped flow traces were recorded for each sample.

Figure 6:
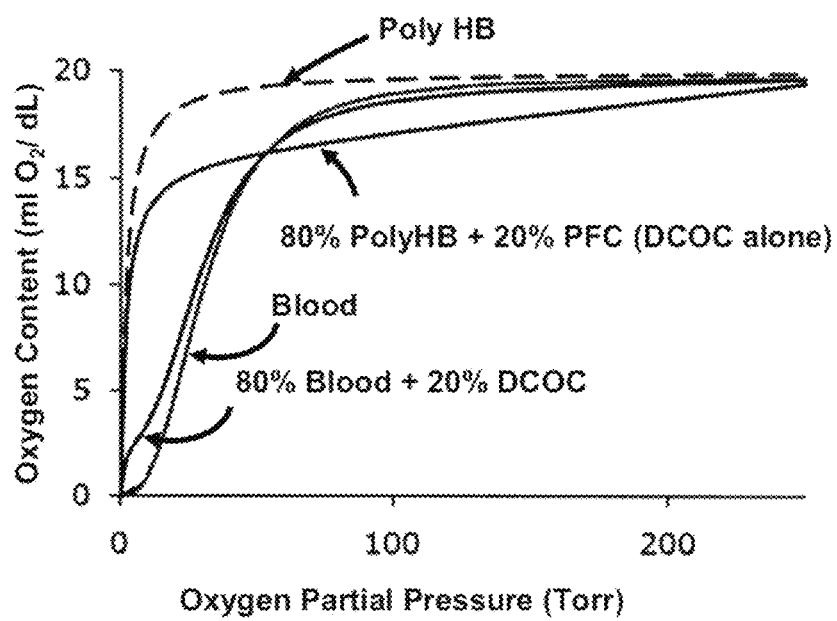
FIG. 6 is a graph showing the oxygen content vs oxygen partial pressure of DCOC.

In an alternative embodiment of the single shell coated AOC the carrier particles have a micron or submicron sized double core of PFC and pHb, which is polymerized hemoglobin, that are made using a batch or continuous flow synthetic method using the same techniques to make single coated AOCs. These are referred to herein as double core oxygen carriers (DCOC). FIG. 5 shows a cross sectional diagram of a double shell artificial oxygen carrier (DCOC) and requires several additional sequential synthesizing steps to those required for making single shell AOCs. Those additional steps are the formation of a stable PFC emulsion, a first shell of a rigid inorganic layer adjacent to the emulsifier, layer by layer synthesis of poly-hemoglobin on the first shell, and a final rigid inorganic shell formation to cover the PolyHB. In addition, FIG. 6 shows how good the DCOC oxygen carrier performs as a blood substitute, as previously mentioned. Other than polyHb other Hb monomers, genetically modified Hb, and Hb from bovine and human sources may also be utilized.

The DCOC delivers oxygen and extracts carbon doxide and, because of its high density, it can be retrieved using continuous flow density gradient separation from the circulating blood that has been previously described with respect to single shell AOCs. The oxygen dissociation curve of DCOC can be made similar to that of the normal blood, thus, unlike perfluorocarbon based oxygen carriers, it does not required additional use of oxygen tank by the patients. It remains in circulation, is strong enough to withstand turbulence in the blood circulation, and has sufficiently fast permeability to exchange gases in the lungs and tissue. Having two different kinds of oxygen carriers—PFC and Hb, the toxicity of DCOC is smaller than those made of a single component.

1,2-dioleoyl-snglycero-3-phosphate (DOPA) and PFC such as perfluoroctyl bromide or perfluorodecalin of density near 2.0 g/ml are mixed and extruded through porous membranes of a selected diameter to form an PFC emulsion with submicron size. The emulsion is suspended in a 15 mM phosphate buffer solution at pH values between 8-9 and to the suspension 100 mM $CaCl_2$ solution is slowly added to form a thin layer of dicalcium phosphate dihydate (DCPD) to the submicron size PFC emulsion particles to stabilize them. Next, the DCPD shell surface of the DCOC particles is carboxylated with carboxyethylphosphonic acid (CEPA) to prevent aggregation of the particles, to stop further growth of the DCPD shell, and to inhibit self-aggregation of the particles at physiological pH. The thickness of the DCPD shell is typically kept between 3-15 nm by controlling the duration of the DCPD formation and removing the unreacted reagents by dialysis or centrifugal membrane filtration. The density of the finished particles is about 1.8 g/ml and thus they can be concentrated easily through centrifugation up to 50% volume. Preliminary studies have shown that the shelled PFC particles are stable in phosphate buffered saline, withstand turbulence equivalent to what is expected in the blood and exhibit a rate of exchange of oxygen faster than what is expected of red blood cells (RBC).

The PFC particles with DCPD shell may be tagged with a fluorescent marker for tracking and quantitative analysis. One O10 1-Palmitoyl-2-[12-[(7-nitro-2-1,3-benzoxadiazol-4-yl) amino]dodecanoyl]-sn-Glycero-3-Phosphocholine (1 6:O-12:O NBD PC) will be mixed with the DOPA and used to complete the synthesis of PFC emulsion as described above. Knowing that NBD is excited at 460 nm and fluoresces at 534 nm, and calculating the number of emulsion particles present in suspension, a calibration curve may be constructed for each lot of DCOC, with which the amount of particles an unknown sample constructed using such an emulsion may be estimated. When the emulsion is mixed with RBC, excitation and emission of both samples will interfere with each other and the estimated concentration of each sample will require solving a simultaneous equation of absorption and emission spectra. To reduce the error a hydrophobic fluorescent dye (whose absorption and fluorescence will be least interfered with by the RBC) is utilized as the marker.

The next step in synthesizing DCOC is to add a second oxygen/carbon dioxide carrying layer. This is done by depositing a layer of polylysine/Hb over the PFC particles with DPCD shell therebetween. The DPCD layer is treated with CEPA to prevent further CaP deposition and to carboxylate the CaP surface of the shell. Polylysine/Hb is deposited electrostatically layer by layer onto the negatively charged carboxylated surface of the DCPD shell made in the previous step of the process. The polylysine is inherently positively charged and Hemoglobin is inherently negatively charged during the method of making the particles. The Hb shell is not continuous for example. The hemoglobin may be small globules of polyhemoglobin embedded in polylysine deposited in layers which is tethered to a layer or shell of calcium phosphate (the inorganic layer) which acts as a continuous shell or layer.

The first step is to cover the surface of the DCPD/CEPA coated PFC emulsion, described in the previous paragraphs, with a molecular layer of polylysine. Polylysine adheres electrostatically to charged surfaces and other proteins and is generally accepted safe as a food additive by the U.S. Food and Drug Administration. For firm adhesion, the length of the polylysine molecules should be sufficiently long to span at least 3 or more hemoglobin molecules. Assuming that the diameter of hemoglobin is approximately 4 nm and the length of monomeric lysine is about 1 nm, to synthesize polylysine/Hb, we will need at least a 12-mer of polylysine. However, the length of the polylysine molecules may be increased to stabilize the Hb. On the surface of a 200 nm diameter PFC particle there is enough space to attach as many as 24,000 Hb molecules. If 50% or more of the surface is to be coated with Hb, and it requires at least 4 polylysine molecules to hold down an Hb molecule, 48,000 polylysine molecules must be attached to the surface of a PFC particle having the first shell thereon. If the concentration of PFC particles is known, the minimum number of polylysine molecules needed for the coating can be estimated. The deposition of polylysine (and Hb) can be monitored using zeta potential measurements throughout the course of the process, and confirmed spectroscopically or by total carbon content after removal of excess reagents from the mixture by dialysis. Polymers other than polylysine may also be utilized, such as polyethylene glycol, polylactic acid, polyglycolic acid pHEMA, chitosan, and chondroitin.

Once the first layer of polylysine is deposited, a hemoglobin (Hb) solution containing at least 12,000× the concentration of the PFC particles is added as the first layer of Hb to polymerize. This is followed by 3-4 times the concentration of polylysine. Alternating addition of Hb and polylysine will continue until the desired thickness of the polylysine/Hb layer is attained. All the reactions will be carried out at pH 8 so that the oxidation of Hb is kept low and opposing ionic charges are maintained between Hb and CEPA.

Once the polylysine/Hb layer is completed, a second and final DCPD and CEPA coating is applied to strengthen the DCOC particle. This final layer also serves to keep the inner materials intact. A detailed cross-section of the DCOC so produced is shown in FIG. 5 and FIG. 8.

In FIG. 6 a graph showing the oxygen carrying ability of a double core oxygen carrier (DCOC) is illustrated. The DCOC alone having 80% Poly HB and 20% PFC inside its shells is very close to that of whole blood, and when the same DCOC is added to blood to make up 80% blood and 20% DCOC it also has an oxygen carrying capability that is very close to that of whole blood. The oxygen carrying ability of Poly HB alone is also shown.

More particularly, the graph in FIG. 6 illustrates the oxygen dissociation curve of the blood, hypothetical oxygen dissociation curves of isolated components used to synthesize dual core oxygen carriers (DCOC), i.e. pHb and PFC, and the numerically added oxygen dissociation curves of 80% pHb and 20% PFC and similarly 80% the blood and 20% DCOC. It is noted that the oxygen dissociation curves of the blood and the DCOC and blood mixture are similar in their sigmoidal nature and oxygen affinity, suggesting that both can transfer nearly equal amounts of oxygen from the lungs to the tissue. In other words, unlike PFC based AOC, supplemental oxygen inhalation by the patients may be no longer needed. Furthermore, it may also contribute to reduce the rate of oxidation of pHb and inhibit its direct contact with the environment, avoiding some of the problems associated with currently developed pHb products.

Various configurations of AOCs that are CEPA-functionalized on the outer surface of the DCPD layer and to which an additional substance(s) are cross-linked to the free carboxylic acid group of CEPA_x are envisioned. A surface activated layer of an individual retrievable particle can be a protein such as an antibody crosslinked to the CaP layer or other biochemically active substance such as a chelator, enzyme, nucleic acid etc. using various crosslinking reagents such as EDC/SNHS (Pierce). The activated surface may be high density or low density. The activated layer can also be a polymer layer, such as polylysine, polyethylene glycol or polylacticpolyglycolic acid, pHEMA etc (available from Sigma). Many of these materials are known in the literature as being used to coat other type of nanoparticles and provide other functionality. They would be complementary to our retreivability feature but are not exclusive to this technology. The activated layer can also be a layer of crosslinked hemoglobin and polyelectrolytes, or consist of another non-retrievable nanoparticle or material with other properties such as magnetic and chemical-activity.

There are different ways of packaging the retrievable particles, tethered in pairs or larger numbers. To generate these type of particle arrangements the active surface would have the property of crosslinking particles together using standard crosslinking chemistries. For example, avidin-biotin, antibody-antigen, or direct crosslinkers may be used. These strategies are also used in the literature and provide a complementary enhancement to our retrievable particles by increasing their mass or combining multiple formulations of retrievable particles which may have different detection ability (for example combining fluorescently tagged and MRI active retrievable nanoparticles, or combining non-retrievable probe nanoparticles with a retrievable nanoparticle to have both probe features and retrievability features, or combining paramagnetic nanoparticles or material with of the high density retrievable particles in order to use both density and magnetic susceptibility for the retrieval).

The AOC (either single shell or double shell) particles can be retrieved from circulating blood using the same continuous flow, density gradient separation that is used for single coat AOCs. This is due to its density being higher than the density of red blood cells. Typically, the AOC is retrieved from a patients system as soon as its medical purpose is accomplished in order to alleviate the physiological stress on already compromised patients.

The AOC is designed for the rough service of being circulated through the body and through continuous flow density gradient system such as a closed loop fluid aphaeresis system without breaking down and being retrievable. More particularly, the AOC is designed to be continually circulated in a closed loop fluid circulation system, are not subject to turbulent breakup, chemical decomposition, or accumulation of debris, and they do not release their payloads, but are capable of exchange of small ions and gases, and which can be retrieved at any time desired using continuous flow separation employing density-gradient centrifugation, which may be supplemented with magnetic fields, affinity filtration or other methods, without suffering damage, or inflicting damage on other materials that may already be present in the flowing fluid.

Other applications for the novel AOC include removal and concentration of metastatic cancer cells from circulating blood, retrieval of low copy mammalian, bacterial or virus cells, and tissue and organ imaging. Depending on the application, the specific design requirement of these materials in terms of their size and composition may vary, but common to all of them are the properties summarized earlier, and the tailored ability for continuous retrieval from circulating fluids.

To remove the AOC particles from the blood one or more of the following continuous flow separation methods may be used: (a) centrifugation, (b) magnetic fields, and/or (c) affinity filtration without suffering damage or inflicting damage on other materials that may already be present in the flowing fluid.

Figure 7:
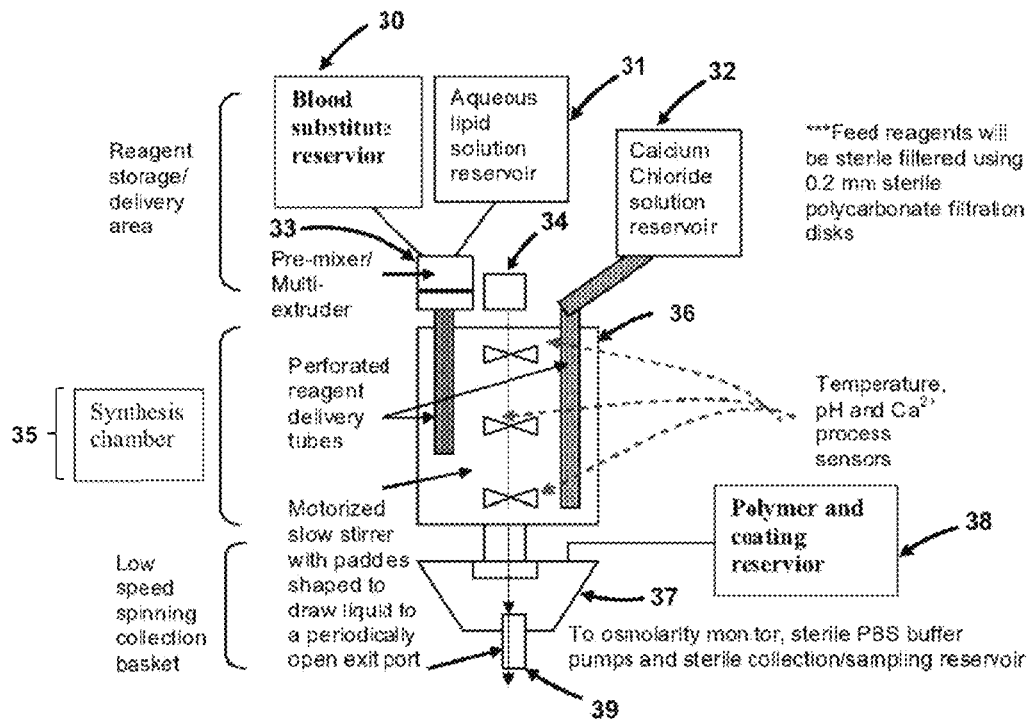
FIG. 7 is a block diagram showing the assembly of systems used for continuous synthesis of stabilized artificial oxygen carriers (AOC and DCOC)

FIG. 7 is a block diagram showing the assembly of systems used for continuous synthesis of stabilized artificial oxygen carriers (AOC and DCOC). Details of the materials used in the synthesis have previously been described in detail in this Detailed Description. The steps, materials, percentages, of the process have been previously described in detail so are not repeated here. The overall system comprises controllable sources for delivering the raw materials and include a reservoir of PFC as a blood substitute 30, a reservoir 31 of an aqueous lipid solution such as DOPA or lecithin or other lipid, and a reservoir 32 of a prepared calcium chloride (CaCl) solution. There is a pre-mixer/multi-extruder 33 into which the materials in reservoirs 30 and 31 are controllably gated under computer control. Pre-mixer/multi-extruder 33 creates nano-emulsion particles as previously described in this Detailed Description. The nano-emulsion particles are delivered via a perforated reagent delivery tube into a synthesis chamber 35 and, at appropriate times, calcium chloride solution is also added to the synthesis chamber to create the reinforcing shell 12 around the emulsion particles 13. The raw materials in chamber 35 are slowly stirred by motor 34 driven paddles 36 during the coating process.

At an appropriate time the coated nano-emulsion particles exit synthesis chamber 35 into rotating basket/finishing reactor 37 where the particles are coated with CEPA 18. In basket 37 the coated nano-emulsion particles are slowing stirred with enough CEPA 18 to coat the available surface area of the particles. As previously described the CEPA coating carboxylates the particle surface, stops further growth and inhibits self-aggregation of the nano-emulsion particles at physiological pH. After exiting finishing reactor at point 39 the particles are concentrated centrifugally (not shown) to higher than 50 vol % and the final product is dialyzed against phosphate buffered saline using 100,000 MWCO Spectrapore dialysis tubing (Pierce) and sterilized by autoclaving without any damage to the particles. The concentrated emulsion nanoparticles 13 are collected in a sterile reservoir (not shown). The osmolarity of the collected final AOC nanoparticle 11 is measured and adjusted with sterile PBS if necessary. Although a calcium based shell is mentioned here, other materials may be used to form the shell 12 such as a silicate, or biocompatible organic polymers such as, polycaprolactone, polylactic acid, polyglyocolic acid, polyethylene oxide, chitosan or chondroitin.

The lipid solution in reservoir 31 preferably may have lecithin therein for the reasons previously described. In addition, paramagnetic materials may be added to the higher density PFC in each nanoparticle, and the magnetic susceptibility is used later for the retrieval of the polymerized hemoglobin. The flowing liquid containing paramagnetic and diamagnetic materials (the natural blood component) must be exposed to a magnetic field during the centrifugal separation so that they will deviate in the direction of the flow of particles with paramagnetic materials away from the diamagnetic particles, thus making it possible to separate and collect both types of particles.

Referring now to FIG. 8 is the cross sectional view of an AOC with the hypothetical $PO_2$ levels inside the particle, while it is transferring $O_2$ to the tissue. The central region of the PFC is well saturated with $O_2$, though its diffusive transport is slow. The PFC is protected and only its surface CEPA will interact with the lysine supported Hb on the right. In this region the transport of oxygen will be fast, due to the facilitated $O_2$ transportation by chemically active hemoglobins. As a consequence, $O_2$ demands by the tissue on the surface of the particles will be met and the $PO_2$ at the edge will be lowered quickly. As soon as the particles leave the tissue capillaries the PFC can refurbish the level of $PO_2$ in the Hb region. And eventually in the lungs, the procedures will be reversed to saturate PFC and Hb with $O_2$. The core of the carrier nanoparticle is represented by the element at the far left of the figure with the exterior represented by the element at the far right. The layers from left to right may be: PFC-DOPA-DCPD-CEPA-(POLY-LYSINE$_m$/polyHB)$_n$-DCPD-CEPA-ACTIVE SURFACE LAYER wherein m represents the number of lysines in the polymer and n represents the number of hemoglobin monomers in the aggregate. It is noted that hemoglobin monomers may be substituted for the polyHemoglobin. DOPA may be substituted for lecithin or a combination of the two may be present. An imaging tracer can be added to the nanoparticle upon formation for convenience and tracking of the nanoparticle in use.

The PFOB at the central core offers a large oxygen capacity and the Hb at the layer outside of the PFOB central core transports this oxygen to the outside of the particle quickly through typical facilitated transport of oxygen through the hemoglobin embedded in the polylysine matrix involving quick chemical reactions between O2 and Hb according to the oxygen gradient resulting in the fast delivery of oxygen to the outside of AOC. Under this orchestrated performance of PFOB, Hb and O2, we will have efficient oxygen carrier, using effective the entire oxygen carried in the particle, responding to the level of needs of the tissue. (Lysine)n is between 10-5000 units of lysine or 2-20000 units of lysine. The fewer the units the smaller the pore size of the polylysine matrix while the higher number of units provides larger pore size. The Hb has greater degree of mobility when embedded in a polylysine made with more units as compared to less units of lysine.

While what has been described herein is the preferred embodiment of the invention and some alternative embodiments it will be understood by those skilled in the art that numerous changes may be made without departing from the spirit and scope of the invention. As used herein "a" or "the" means one or more. All references cited herein are incorporated by reference for all purposes.

What is claimed is:

1. A particulate artificial oxygen carrier for use as a blood substitute, the particulate artificial oxygen carrier comprising:
    a PFC material that can carry oxygen and carbon dioxide alike blood, and is emulsified to form a core of a carrier nanoparticle with an amphiphile emulsifier surrounding the PFC material;
    a first rigid inorganic shell formed around the core of the carrier nanoparticle wherein the first rigid inorganic shell is calcium phosphate;
    a layer on the outside of the first rigid inorganic shell, the layer being formed of a Hemoglobin embedded in a matrix of polylysine where the matrix of polylysine is bound to the first rigid inorganic shell wherein the Hemoglobin can transport oxygen and carbon dioxide alike blood; and
    a second rigid inorganic shell around the polylysine/Hemoglobin layer wherein the second rigid inorganic shell is calcium phosphate;
    wherein the particulate artificial oxygen carrier has a higher density than any components of blood, and wherein the first rigid inorganic shell and the second rigid inorganic shell permit the particulate artificial oxygen carrier to be continuously circulated in a person's blood in a closed loop circulation system without releasing the PFC material inside the first rigid inorganic shell and the Hemoglobin embedded in the matrix of polylysine into the blood.

2. The particulate artificial oxygen carrier of claim 1 wherein the amphiphile emulsifier is phosphatidic acid, phosphatidylcholine or a combination thereof.

3. The particulate artificial oxygen carrier of claim 1 wherein the amphiphile emulsifier is lethicin or DOPA.

4. The particulate artificial oxygen carrier of claim 1 further comprising a layer of carboxyethylphosphonic acid between the first rigid shell and the matrix of polylysine layer, the carboxyethylphosphonic acid forming a bond with the calcium phosphate to stop further growth of the first rigid inorganic shell.

5. The particulate artificial oxygen carrier of claim 1 wherein the Hemoglobin is a monomer.

6. The particulate artificial oxygen carrier of claim 1 wherein the Hemoglobin is a polymer of 2-10 Hemoglobin monomers to form a Hemoglobin aggregate.

7. The particulate artificial oxygen carrier of claim 1 wherein the Hemoglobin is not disulfide bonded to itself or another chemical entity.

8. The particulate artificial oxygen carrier of claim 1 wherein the Hemoglobin can diffuse within the matrix of the polylysine.

9. The particulate artificial oxygen carrier of claim 1 wherein the Hemoglobin is electrostatically associated with the polylysine matrix.

10. The particulate artificial oxygen carrier of claim 1 wherein the Hemoglobin is a Hemoglobin aggregate which is electrostatically associated with the polylysine matrix.

11. A method for making a particulate artificial oxygen carrier of claim 1 for use in place of blood in a person, the method comprising the steps of:
    emulsifying a PFC material with an amphiphile emulsifier wherein the emulsified PFC material can carry oxygen and carbon dioxide alike blood;
    forming the emulsified PFC material into a core of a carrier nanoparticle;
    coating the core of the carrier nanoparticle with a calcium phosphate layer to form a first rigid inorganic shell around the core of the carrier nanoparticle, the first rigid inorganic shell being permeable to oxygen and carbon dioxide;
    forming a layer on the outside of the first rigid inorganic shell, the layer being formed of a Hemoglobin embedded in a matrix of polylysine where the matrix of polylysine is indirectly bound to the first rigid inorganic shell wherein the Hemoglobin can transport oxygen and carbon dioxide alike; and
    coating the polylysine/Hemoglobin layer with calcium phosphate to form a second rigid inorganic shell around the polylysine/Hemoglobin layer;
    wherein the particulate artificial oxygen carrier has a higher density than any components of blood, and wherein the first rigid inorganic shell and the second rigid inorganic shell permit the particulate artificial oxygen carrier to be continuously circulated in a person's blood in a closed loop circulation system without releasing the PFC material inside the first rigid inorganic shell and the Hemoglobin embedded in the matrix of polylysine into the blood.

12. The method for making a particulate artificial oxygen carrier for use in place of blood of claim 11 further comprising the step of coating the first shell with a molecular monolayer to stop the growth of the first rigid inorganic shell.

13. The method for making a particulate artificial oxygen carrier for use in place of blood of claim 11 further comprising the step of coating the outside of the second rigid inorganic shell with a molecular monolayer to stop the growth of the second rigid inorganic shell.

14. The method for making a particulate artificial oxygen carrier for use in place of blood of claim 11 wherein the amphiphile emulsifier is selected from a phosphatidic acid, a phosphatidylcholine or a combination thereof.

15. The method of claim 11 wherein the Hemoglobin is a monomer.

16. The method of claim 11 wherein the Hemoglobin is a polymer of 2-10 Hemoglobin monomers to form a Hemoglobin aggregate.

17. The method of claim 11 wherein the Hemoglobin is not disulfide bonded to itself or another chemical entity.

18. The method of claim 11 wherein the Hemoglobin can diffuse within the polylysine matrix.

* * * * *